United States Patent [19]
Jones

[11] 4,004,603
[45] Jan. 25, 1977

[54] GAS VALVE MECHANISMS
[75] Inventor: Norman Stewart Jones, Leighton Buzzard, England
[73] Assignee: Pneupac Limited, London, England
[22] Filed: May 2, 1975
[21] Appl. No.: 574,097
[30] Foreign Application Priority Data
June 4, 1974 United Kingdom ............ 24786/74
[52] U.S. Cl. ............................ 137/107; 128/145.8; 137/543.17; 137/DIG. 9
[51] Int. Cl.² .................. F16K 15/02; A61M 16/00
[58] Field of Search ............ 137/102, 107, DIG. 9, 137/542, 543.17; 128/145.5, 145.8

[56] References Cited
UNITED STATES PATENTS

| | | | |
|---|---|---|---|
| 2,301,276 | 11/1942 | Gussick | 137/542 |
| 3,025,869 | 3/1962 | Kenfield | 137/102 |
| 3,176,624 | 4/1965 | Sundholm | 137/543.17 X |
| 3,451,415 | 6/1969 | Buford et al. | 137/102 |
| 3,606,905 | 9/1971 | Fehler | 137/107 |
| 3,672,366 | 6/1972 | Burchell | 137/102 X |

FOREIGN PATENTS OR APPLICATIONS 622,904  5/1949  United Kingdom ............... 137/102

Primary Examiner—Robert G. Nilson
Attorney, Agent, or Firm—Kurt Kelman

[57] ABSTRACT

A gas valve mechanism especially suitable for use as the patient valve in conjunction with a lung ventilator or resuscitation device by developing high actuating forces from low pressure gas supplies comprises a valve element movable in a body having a gas pulse inlet, a gas pulse outlet and an exhaust outlet. The valve element has a large effective area exposed to the gas pulse inlet and is moved by gas pressure at that inlet, against spring-loading, to open a restricted flow path to the gas pulse outlet, the flow path restriction developing a pressure differential acting to oppose the spring loading and hold the valve element positively in the flow path open position.

8 Claims, 2 Drawing Figures

GAS VALVE MECHANISMS

FIELD OF THE INVENTION

This invention concerns gas valve mechanisms and more particularly valve mechanisms for controlling the connection of a gas pressure pulse source to a pulse outlet. Valve mechanisms having this function are, for instance, used in conjunction with lung ventilation and resuscitation devices for controlling the connection of a ventilator to the respiratory passages of a patient; in such applications, the valve mechanism — often called a "patient valve" — serves to connect the respiratory passages of the patient to the ventilator during an inhalation phase and to an exhaust outlet during the exhalation phase.

BACKGROUND OF THE INVENTION

Hitherto the valve mechanisms designed for such applications have been of two types: the low-pressure type adapted for actuation by the low-pressure pulses produced by most types of ventilator; and the high-pressure type intended for use with certain ventilators capable of producing appropriately high-pressure pulses. As hitherto designed, valves of the low-pressure type have suffered from the major defect of being designed to develop very small forces to effect their changeover, the valves being therefore delicate and prone to failure as a result of minor damage or distortion of their components by handling — e.g. during sterilisation procedures — and, especially, as a result of clogging by foreign matter entering the valve mechanism — for instance, vomit, etc. exhaled by the patient in emergency situations. On the other hand valves of the high-pressure type, while being generally more robust and less likely to be prevented from operation by the ingress of foreign matter, have the disadvantage of requiring the ventilators with which they may be associated to produce pulses of sufficiently high pressure to effect proper operation of the valves.

An object of the present invention is to provide a valve mechanism that is particularly suited for use as a "patient valve" in conjunction with lung ventilating equipment, and that while actuable by low-pressure pulses derives relatively high force levels from such pulses for actuating its moving elements so as thereby to resist obstruction and impediment by foreign matter that may enter the mechanism.

THE INVENTION

Valve mechanism in accordance with the present invention comprises a body providing a gas pulse inlet, a gas pulse outlet and an exhaust outlet and housing a valve element having a large effective area exposed to said pulse inlet and movable, against spring loading, by pressure thereat to open communication between said inlet and said pulse outlet while interrupting communication between said pulse outlet and said exhaust outlet, the flow path between said pulse inlet and said pulse outlet controlled by the valve element including a restriction to establish a pressure differential acting on the valve element to oppose said spring loading in the case of gas flow from said inlet to said pulse outlet.

The area of the valve element exposed to said pulse inlet is preferably such that with a pressure at said inlet not greater than 0.15 bar, the force on the valve element, in excess of the opposing spring loading, is at least 0.25 kg.

The valve element may be a diaphragm but is conveniently in the form of a piston reciprocable within a cylinder formed in said body and one end of which provides the said pulse inlet and the other end of which provides the said exhaust outlet, the pulse outlet being provided by a lateral branch having at least one port communicating with the cylinder bore within the stroke limits the piston. The arrangement may be such that with the piston in one end position in which it interrupts communication between the pulse outlet and the exhaust outlet, it establishes communication between the pulse inlet and the pulse outlet via a small-area port, in the cylinder wall, that provides a restriction in the flow path between the pulse inlet and the pulse outlet. This restriction may, however, be provided elsewhere in the said flow path and is conveniently provided by a suitably sized aperture in the piston.

The pulse outlet is preferably in permanent communication with a relief valve adapted to prevent pressure in the pulse outlet rising above a predetermined value.

Preferably the complete valve mechanism is designed to be dismantled and reassembled without possibility of misassembly and without the use of tools, to facilitate its cleaning and sterilisation for use as a "patient valve" and preferably all parts are constructed of material that will withstand conventional sterilisation procedures without deterioration.

In preferred forms of the mechanism in which the exhaust outlet is at one end of the body, the valve element preferably engages a seat constituted by an annular surface surrounding said exhaust outlet so as to be held on said seat by the force balance acting on the valve element when there is pressure at said pulse inlet: accordingly the higher the pressure at the pulse inlet, the greater will be the seat-engaging force to prevent leakage through the exhaust outlet. Leakage from the pulse inlet to the exhaust outlet can, therefore, normally only occur when the valve element is moving between its stroke-end positions. In such embodiments, therefore, the valve element may have large clearances in the housing and therefore be relatively immune to jamming as a result of minor distortion or the ingress of foreign matter.

THE DRAWINGS

FIG. 1 is an axial sect ional view of a preferred form of valve mechanism for use as a patient valve with lung ventilation equipment; and FIG. 2 is a part-sectional end view, at the pulse inlet, of the valve mechanism of FIG. 1.

DESCRIPTION OF PREFERRED EMBODIMENT

Figure 1:
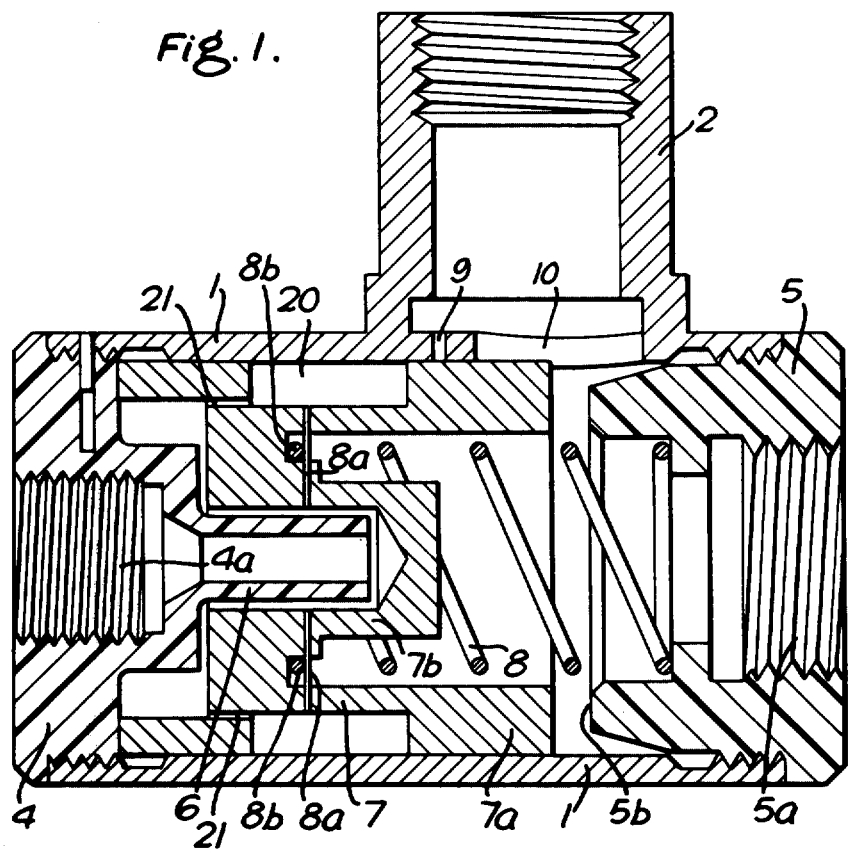
Figure 2:
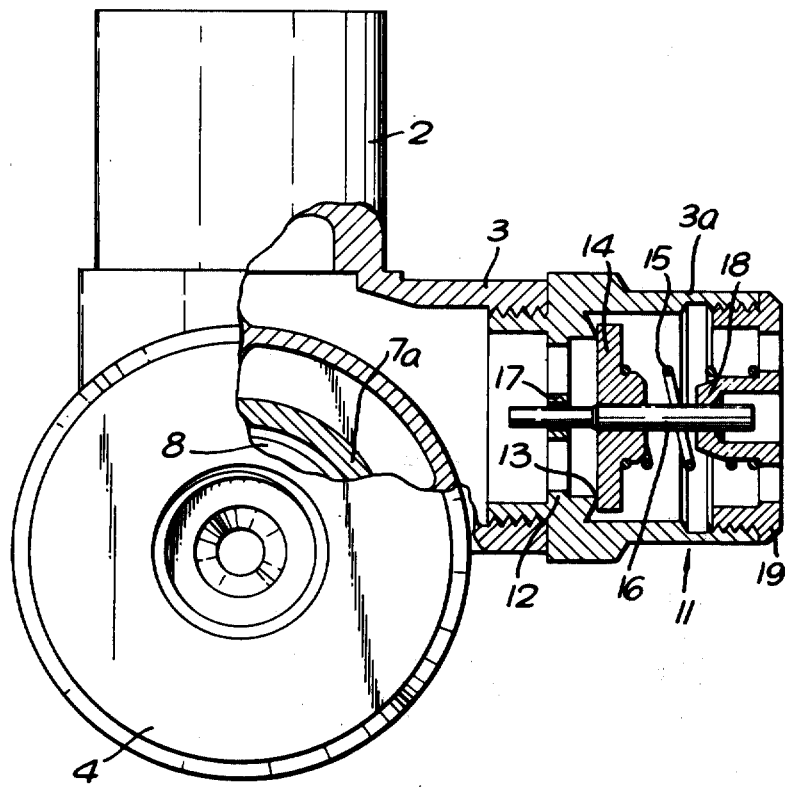

In the embodiment shown in the drawings, the valve mechanism comprises a tubular housing 1 having lateral branches 2,3 and its ends closed by plugs 4,5. The housing is constructed of metal or plastics material capable of sterilization and the plugs are preferably constructed of a similar plastics material but may be constructed of metal. The plugs are of stepped construction with external screwthreads on their smaller diameters mating with internal screwthreads in the respective ends of the housing 1. The plug 4 is secured permanently in place by a pin pressed into aligned radial bores in the plug and housing end.

The plug 4 has a central pulse inlet opening 4a to receive a conduit connection from a source of gas pressure pulses, e.g. a lung ventilating machine, and a central tubular spigot 6 on its inner face for a purpose to be described.

The plug 5 is tubular with a central opening 5a defined by an internal flange in its bore and provides an exhaust outlet for the valve mechanism.

The housing 1 defines a cylinder within which a spool-like piston 7 is reciprocable, the piston 7 being formed of metal or a sterilizable plastics material and having a hollow head 7a with a central opening through which a helical compression spring 8 extends, one end of the spring 8 engaging an abutment surface deep within the piston 7 and being held captive by a pair of pins 8a that extend over diametrically opposed portions of the final turn 8b of the spring. The turn 8b of the spring preferably terminates in a turned-up tag (not shown) to prevent the turn 8b of the spring being "unscrewed" from under the pins 8a. The other end of the spring 8 engages the inner face of the flange defining the opening 5a in the end plug 5. The spring 8 loads the piston 7, e.g. with a force of at least about 0.25 kg, so as to tend to move the piston to the left as seen in the drawing, but because the spring has a substantial length in comparison with the permitted stroke of the piston 7 and is of low rate, it exerts substantially constant spring loading on the piston throughout the stroke of the latter.

The side branches 2,3 of the housing communicate with one another and with the bore of the cylinder defined by the housing 1 via ports 9 and 10, the port 9 being of smaller cross-sectional area than the port 10 and being positioned to be covered by the head 7a of the piston 7 when this is in its lefthand stroke-end position as seen in the drawing. Although shown as facing the pulse outlet branch 2, the port 9 preferably faces the branch 3 so that the gas stream emitted through the port serves to sweep any foreign matter clear of the branch 3. When the piston 7 moves to its righthand stroke-end position the port 9 is uncovered to establish communication between the pulse inlet 4a of the plug 4 and the side branch 2 that constitutes the pulse outlet of the valve mechanism.

The port 10 provides permanent communication between the side branch 2 and the righthand end of the cylinder defined by the housing 1, irrespective of the position of the piston 7 therein.

The righthand end face of the head 7a of the piston 7 is arranged to cooperate with a seat surface 5b on the inner end of the plug 5 so that when the piston 7 is in its righthand stroke-end position, communication between the side branch 2 and the exhaust outlet opening 5a is interrupted.

The side branch 3 of the housing is fitted with a relief valve assembly 11, arranged to relieve excess pressure arising in the side branch 2. The assembly 11 comprises a tubular body 3a screwed into the end of the side branch 3 and having a ported inner wall 12 surrounded by an annular seat 13 engaged by a valve poppet 14 urged against the seat 13 by a spring 15. The valve 14 has a central stem 16 supported for endwise movement in suitable bearings 17,18 in the wall 12 and in a ported end plug 19 respectively.

The lefthand end of the piston 7 as seen in the drawing has a central boss 7b with an axial recess that fits with substantial clearance over the spigot 6 of the plug 4. The purpose of the spigot 6 and the recessed boss 7b of the piston 7 is to preclude misassembly of the valve mechanism, e.g. after sterilisation, with the piston 7 reversed in the housing 1.

The lefthand end of the piston 7 has small openings 21 that provide restricted communication between the lefthand end of the housing 1 and the annular area 20 surrounding the waist of the piston 7, so that when the piston is in its righthand stroke-end position a restricted flow path is provided from the pulse inlet 4a in the plug 4 via the openings 21 to the port 9 and thence to the pulse outlet constituted by the side branch 2.

In use of the illustrated valve mechanism as a "patient valve" in association with the lung ventilating equipment, the side branch 2 is suitably connected to the respiratory passages of the patient, e.g. by means of an oronasal mask or an intratracheal tube. The pulse inlet 4a is suitably connected to a lung ventilator of any appropriate design that produces pressure pulses of oxygen or other gas. Typically such a ventilator would be capable of producing pulses having a pressure about 0.15 bar and thus be of the common low-pressure pulse class of such devices. The mechanism is, of course, capable of use with ventilators producing higher pulse pressures.

In the quiescent condition of the valve mechanism, the piston 7 is at the lefthand stroke-end position as seen in the drawing, being held in this position by means of the spring 8. In this position, the port 9 is obturated by the piston head 7a so that the interior of the housing to the left of the piston head 7a is isolated from the respiratory passages of the patient, and thus protected from ingress of foreign matter such as vomit, etc. exhaled by the patient.

When a gas pressure pulse arrives at the inlet 4a in the plug 4, gas passes through the spigot 6 and the clearance space between the latter and the recess in the piston boss 7b, and enters the lefthand end of the cylinder defined by the housing. Because at this time there is no outlet from such end of the cylinder, pressure builds up rapidly therein, acting on the substantial effective cross-sectional area of the lefthand end of the piston 7 to cause this to experience a sharply rising force that rapidly overpowers the loading of the spring 8 and moves the piston to its righthand stroke-end position. Even with a pulse pressure as low as 0.15 bar the net force acting on the piston 7 will be at least 0.25 kg and may reach nearly 2 kg if the piston fails to commence moving to the right as soon as the force thereon exceeds that due to the loading of the spring 8 — for instance, as a result of being jammed by foreign matter that has penetrated the righthand end of the cylinder through the port 10. Thus a substantial force may be built up to drive the piston to the right in the presence of contamination impeding free movement of the piston.

When the piston reaches its righthand stroke-end position its head 7a engages the seat surface 5b to close off communication between the pulse outlet branch 2 and the exhaust outlet opening 5a in the plug 5, while the port 9 is uncovered so that gas entering through the inlet 4a flows via the openings 21, the space 20 and the port 9 to the pulse outlet branch 2 and thence to the respiratory passages of the patient.

While gas is flowing through this flow path, the flow restriction offered by the relatively small cross-sectional areas of the openings 21 ensures the maintenance of a pressure differential acting on the piston 7 to hold this in its righthand stroke-end position. However, as the pressure pulse at the inlet 4a decays, this pressure differential decreases to the value at which it produces a force less than that of the spring 8 which, accordingly, then moves the piston back to its lefthand stroke-end position to obturate the port 9 and open communication between the pulse outlet branch 2 and the exhaust outlet opening 5a.

As noted, the side branch 3 is fitted with a pressure relief valve assembly 11, the function of which is to prevent dangerous pressures building up in the outlet branch 2 in the event of, e.g., ventilator failure. The valve assembly 11 also enables the patient to exhale at any time during a ventilation cycle, e.g. as a result of the onset of spontaneous respiration during a resuscitation procedure.

It should also be noted that in the event of a gas supply failure, spontaneous inhalation by the patient is not prevented because in the absence of pressure at the pulse inlet 4a, the valve 7 takes up the lefthand stroke-end position shown in the drawing, providing open communication between the exhaust outlet opening 5a and the pulse outlet branch 2. Moreover, if the valve should stick, e.g. due to failure of spring 8, in the righthand stroke-end position, any pressure reduction at the branch 2, due to an inhalation effort by the patient, will be communicated to the lefthand end of the piston to act on the full effective area thereof while the same pressure only acts on the area outboard of the exhaust opening seat 5b at the righthand end of the piston. Since a higher (atmospheric) pressure acts on the righthand end of the piston inboard of the seat 5b, there will therefore be a substantial net leftward force applied to the piston to move this to open communication between the branch 2 and the exhaust opening.

The exhaust opening 5a in the plug 5 is preferably screwthreaded to enable a conduit to be connected thereto, e.g. for a closed circuit rebreathing ventilator, or to receive an anti-inhalation non-return valve assembly in the case of use of the mechanism in a toxic atmosphere.

The design of the illustrated valve mechanism allows simple dismantling and reassembly for cleaning and sterilisation purposes and it has been pointed out that the design precludes misassembly with the piston 7 reversed within the housing. Further to minimise the possibility of misassembly, the spring 8 has its left end secured to the piston 7 so as to be captive thereby, while, as shown, the design of the pressure relief valve assembly 11 is such that the spring 15 is captive on a hub of the valve 14 and the stem 16 is stepped so as to preclude its being reversed in the bearings 17,18.

I claim:
1. A valve mechanism comprising
   a. a cylindrical body providing a gas pulse inlet, a gas pulse outlet, an exhaust outlet, the gas pulse inlet and the exhaust outlet being at opposite ends of the cylindrical body and the body having lateral branch defining the gas pulse outlet, and the body defining a first flow path between the gas pulse inlet and the gas pulse outlet, the first flow path including a port in the lateral branch, and the first flow path having a constriction, and a second, substantially unrestricted flow path between the gas pulse outlet and the exhaust outlet;
   b. a valve element piston mounted for reciprocation in the body for movement in and controlling said flow paths between a first position wherein the valve element piston interrupts communication between the gas pulse inlet and outlet while opening substantially unrestricted communication between the gas pulse outlet and the exhaust outlet, and a second position wherein the valve element piston opens communication between the gas pulse inlet and outlet while interrupting communication between the gas pulse outlet and the exhaust outlet,
      1. the valve element piston having a large effective area exposed to the gas pulse inlet and a gas pulse pressure at the inlet moving the valve element piston into the second position, and the piston closing the port in the first position and opening the port in the second position;
   c. a spring loading the valve element to hold it in the first position and opposing the movement of the valve element into the second position; and
   d. the constriction in the first flow path establishing a pressure differential acting on the valve element to oppose the spring loading in the second position.
2. The valve mechansim of claim 1, wherein the piston has an aperture sized to provide the constriction in the first flow path.
3. The valve mechanism of claim 1, further comprising an annular seat surrounding the exhaust outlet and facing the piston, the piston engaging the seat in the second position and holding the piston against the seat by the pressure differentail acting on the piston in the presence of the gas pulse pressure at the gas pulse inlet.
4. The valve mechanism of claim 1, the large effective area of the valve piston exposed to the gas pulse inlet being such that, with a gas pulse pressure at the inlet of about 0.15 bar, the force on the valve piston, in excess of the opposing spring loading, is at least about 0.25 kg.
5. The valve mechanism of claim 1, wherein the gas pulse inlet includes a spigot extending into the body and the valve piston includes a central boss having an axial recess fitting with substantial clearance over the spigot, the clearance providing part of the first flow path and the valve piston having an annular aperture between the clearance and the gas pulse outlet to provide the constriction in the first flow path.
6. The valve mechanism of claim 1, wherein the spring is a coil spring, one end of the coil spring being held captive on the valve piston.
7. The valve mechanism of claim 1, further comprising a relief valve in permanent communication with the gas pulse outlet and arranged to prevent pressure in the gas pulse outlet from rising above a predetermined level.
8. The valve mechanism of claim 7, wherein the relief valve comprises a stepped valve stem having two parts of different diameters, a bearing for one valve stem part, a bearing for the other valve stem part, a valve body mounted on the valve stem, and a coil spring acting on the valve body, one end of the coil spring being held captive on the valve body.

* * * * *